United States Patent [19]

Buzas et al.

[11] 4,096,259
[45] Jun. 20, 1978

[54] NON-AMPHETAMINIC PSYCHOSTIMULATING COMPOSITIONS OF 1,4-DISUBSTITUTED PIPERAZINES

[76] Inventors: André Buzas, 25 Route de Versailles, Bievres, Essonne; Jean-Marie Melon, 158 rue de Courcelles, Paris 17eme, both of France

[21] Appl. No.: 684,846

[22] Filed: May 10, 1976

[30] Foreign Application Priority Data

May 13, 1975 France .............................. 75 14804

[51] Int. Cl.² .......................................... A61K 31/495
[52] U.S. Cl. .................................. 424/250; 544/397; 544/377; 544/357; 544/121
[58] Field of Search ................... 260/268 BZ; 424/250

[56] References Cited

U.S. PATENT DOCUMENTS

| | | | |
|---|---|---|---|
| 2,953,568 | 9/1960 | Werner | 260/268 BZ |
| 3,205,134 | 9/1965 | Biel | 424/250 |
| 3,652,568 | 3/1972 | Winter et al. | 260/268 BZ |

FOREIGN PATENT DOCUMENTS

| | | |
|---|---|---|
| 2,073,277 | 10/1971 | France. |
| 2,024,775 | 9/1970 | France. |

*Primary Examiner*—Donald G. Daus
*Assistant Examiner*—D. B. Springer
*Attorney, Agent, or Firm*—Young & Thompson

[57] ABSTRACT

1,4-disubstituted piperazine derivatives having the formula

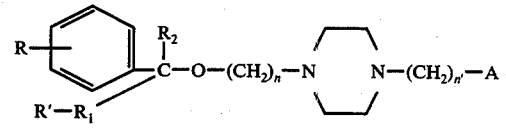

wherein R is $C_{1-3}$ alkyl, halogen or hydrogen; $R_1$ is phenyl or $C_{1-3}$ alkyl; R' is hydrogen when $R_1$ is alkyl and is the same as R when $R_1$ is phenyl; $R_2$ is hydrogen or $C_{1-3}$ alkyl; $n$ is 2–4; $n'$ is 1–4; and A is a group comprising a trivalent organic function which may be acid, ester, nitrile or amide, in which latter case the nitrogen of the amide is part of the ring, and more particularly COOH, COONa, $COOCH_3$ or $COOC_2H_5$. These derivatives or their addition salts with pharmaceutically acceptable acids, have high psychostimulating activity.

4 Claims, No Drawings

NON-AMPHETAMINIC PSYCHOSTIMULATING COMPOSITIONS OF 1,4-DISUBSTITUTED PIPERAZINES

This invention relates to pharmaceutical compositions of non-amphetaminic psychostimulating activity comprising as active substance a 1,4-disubstituted piperazine derivative.

1,4-disubstituted piperazine derivatives are known in which one of the nitrogen atoms of the piperazine is substituted with the benzhydryl or benzhydryloxyethyl group while the second one is substituted either with an alkyl group or with an ether group having the formula:
—$CH_2$—$CH_2$—O—R, R being an alkyl radical, or with an amide group having the formula:

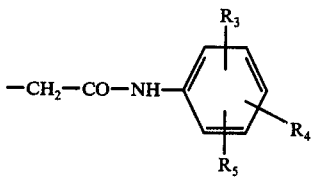

wherein $R_3$, $R_4$ and $R_5$ are hydrogen or halogen atoms, alkyl, alkoxy or trifluoromethyl groups.

These derivatives are known as having antihistaminic, anticholinergic, spasmolytic or sedative properties.

The object of this invention is to provide new pharmaceutical compositions of non-amphetaminic psychostimulating activity comprising as active substance a 1,4-disubstituted piperazine derivative.

The 1,4-disubstituted piperazine derivatives which are the active substance of the pharmaceutical composition of this invention have the following general formula:

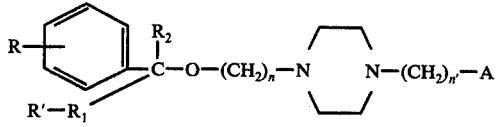

wherein:
R is an alkyl group having less than four carbon atoms, a halogen or a hydrogen atom,
$R_1$ is a phenyl or alkyl group having less than four carbon atoms,
R' is a hydrogen atom when $R_1$ is an alkyl group and has the same definition as R when $R_1$ is a phenyl group,
$R_2$ is a hydrogen atom or a alkyl group having less than four carbon atoms,
n is an integer equal to 2, 3 or 4,
n' is an integer equal to 1, 2, 3 or 4, According to the invention, these derivatives are characterized in that A is a group having a trivalent organic function selected from acid, ester, nitrile or amide functions, the nitrogen of the amide beig part of the ring.

In a first group of derivatives, $R_1$ is a phenyl group. Certain derivatives of this group also have a high spasmolytic activity of the papaverine type.

In a second group of derivatives, $R_1$ is an alkyl group.

The trivalent organic function of group A is selected, preferably, from among the following: — COOH and its alkaline salt, — CN, — $COOCH_3$, $COOC_2H_5$, $COOC_3H_7$, $COOC_4H_9$, $COOC_6H_{13}$,

(carbonylmorpholine)

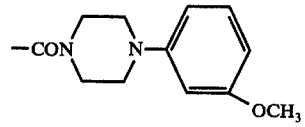

(1-carbonyl-4-(3-methoxyphenyl)-piperazine

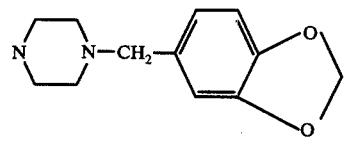

(1-carbonyl-4-(3,4-methylenedioxybenzyl)-piperazine

The groups

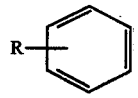

and R'-$R_1$, when $R_1$ is a phenyl group, are selected, preferably, from among the following:
3,4-methylenedioxyphenyl,
3,4,5-trimethoxyphenyl,
2,4-dimethoxyphenyl,
2-methoxy-4-amino-5-chlorophenyl.

As far as the derivatives of the second group are concerned, $R_1$ is preferably an n-propyl group.

The nomenclature of several preferred derivatives of the invention is given below:

DERIVATIVES OF GROUP I:

1-(carboxyethyl)-4-(2-p-fluorobenzhydryloxyethyl)-piperazine
1-(methoxycarbonylbutyl)-4-[2-(4,4'-difluorobenzhydryloxy)ethyl] piperazine
1-(carboxyethyl)-4-(2,0-methoxybenzhydryloxyethyl)-piperazine
1-(hexyloxycarbonylethyl)-4-[2-(4,4'-difluorobenzhydryloxy)-ethyl] piperazine
1-(ethoxycarbonylethyl)-4-(p-fluorobenzhydryloxypropyl)-piperazine
1-(propionitrile)-4-(2-benzhydryloxyethyl)piperazine
1-(morpholinocarbonylmethyl)-4-(2-benzhydryloxyethyl)piperazine
1-(piperonylpiperazinocarbonylmethyl)-4-(2-benzhydryloxyethyl) piperazine

DERIVATIVE OF GROUP II:

1-(ethoxycarbonylethyl)-4-[2-(n-butoxy-1-p-fluorophenyl)-ethyl]piperazine

The invention also relates to the pharmaceutically acceptable acid salts of the derivatives according to the invention and, in particular, to pharmaceutical compositions containing the hydrochlorides, oxalates, maleates and trimethylsulfonates of these derivatives.

In Tables I and II below, are listed several derivatives according to the invention comprising groups I and II. The instaneous melting point (inst. MP) is indicated for each of the derivatives.

TABLE I

Derivatives of group I having the general formula:

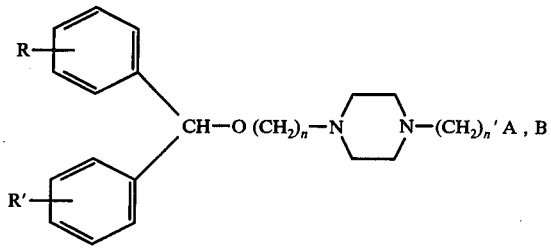

R, R', n, n', A having been defined previously and B being the pharmaceutically acceptable acid associated with the derivative.

| Derivative N° | A | R | R' | n | n' | B | Inst. MP |
|---|---|---|---|---|---|---|---|
| 1 | COONa | H | H | 2 | 1 | | 234° C |
| 2 | COONa | H | H | 2 | 2 | | 260° C |
| 3 | COOH | H | H | 2 | 3 | HCl | 116° C |
| 4 | COOH | H | pF | 2 | 1 | 2C$_4$H$_4$O$_4$ | 148° C |
| 5 | COOH | H | pF | 2 | 2 | 2C$_4$H$_4$O$_4$ | 175° C |
| 6 | COOH | H | m CF$_3$ | 2 | 2 | 2C$_4$H$_4$O$_4$ | 178° C |
| 7 | COOH | H | o OCH$_3$ | 2 | 2 | 2C$_4$H$_4$O$_4$ | 175° C |
| 8 | COOH | H | p Cl | 2 | 2 | 2C$_4$H$_4$O$_4$ | 174° C |
| 9 | COOH | H | p CH$_3$ | 2 | 2 | 2C$_4$H$_4$O$_4$ | 180° C |
| 10 | COOH | H | 3-4-5OCH$_3$ | 2 | 2 | 2C$_4$H$_4$O$_4$ | 168° C |
| 11 | COOH | pF | pF | 2 | 2 | 2C$_4$H$_4$O$_4$ | 180° C |
| 12 | COOH | H | pF | 2 | 3 | 2C$_4$H$_4$O$_4$ | 170° C |
| 13 | COOH | H | pF | 2 | 4 | 2C$_4$H$_4$O$_4$ | 176° C |
| 14 | COOCH$_3$ | pF | p F | 2 | 4 | 2 HCl | 200° C |
| 15 | COOC$_2$H$_5$ | pF | p F | 2 | 1 | 2 HCl | 160° C |
| 16 | COOC$_2$H$_5$ | H | H | 2 | 2 | HCl | 200° C |
| 17 | COOC$_2$H$_5$ | H | o Cl | 2 | 2 | 2 HCl | 180° C |
| 18 | COOC$_2$H$_5$ | H | p Cl | 2 | 2 | 2C$_4$H$_4$O$_4$ | 180° C |
| 19 | COOC$_2$H$_5$ | H | p CH$_3$ | 2 | 2 | 2C$_4$H$_4$O$_4$ | 178° C |
| 20 | COOC$_2$H$_5$ | H | p NO$_2$ | 2 | 2 | 2 HCl | 180° C |
| 21 | COOC$_2$H$_5$ | pF | p F | 2 | 2 | 2 HCl | 190° C |
| 22 | COOC$_2$H$_5$ | pF | p CH$_3$ | 2 | 2 | 2 HCl | 190° C |
| 23 | COOC$_2$H$_5$ | pF | p F | 2 | 3 | 2 HCl | — |
| 24 | COOC$_2$H$_5$ | H | p F | 2 | 3 | 2 HCl | — |
| 25 | COOC$_4$H$_9$ | pF | p F | 2 | 2 | 2C$_4$H$_4$O$_4$ | 180° C |
| 26 | COOC$_6$H$_{13}$ | pF | p F | 2 | 2 | 2C$_4$H$_4$O$_4$ | 174° C |
| 27 | COOC$_2$H$_5$ | H | H | 3 | 2 | 2 HCl | 220° C |
| 28 | COOC$_2$H$_5$ | H | p F | 3 | 2 | 2 HCl | 200° C |
| 29 | CN | H | H | 2 | 2 | 2 HCl | 160° C |
| 30 | CONH$_2$ | H | H | 2 | 2 | 2 HCl | 180° C |
| 31 | CON⟨morpholino⟩ | H | H | 2 | 1 | 2C$_4$H$_4$O$_4$ | 205° C |
| 32 | CON⟨piperazinyl-(o-OCH$_3$-phenyl)⟩ | H | H | 2 | 1 | 2CH$_3$SO$_3$H | — |
| 33 | CON⟨piperazinyl-N-CH$_2$-(methylenedioxyphenyl)⟩ | H | H | 2 | 1 | 3C$_4$H$_4$O$_4$ | 190° C |
| 34 | CON⟨piperazinyl-N-CH$_2$-(methylenedioxyphenyl)⟩ | pF | p F | 2 | 1 | 3C$_4$H$_4$O$_4$ | 150° C |

TABLE II

Derivatives of group II having the general formula:

The letters o, p and m in this Table indicate, respectively, the ortho, para and meta positions of the phenyl radical.

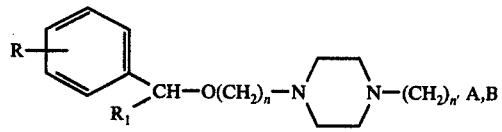

| Derivative N° | A | R | $R_1$ | n | n' | B | Inst. M.P. |
|---|---|---|---|---|---|---|---|
| 35 | COOH | H | $nC_3H_7$ | 2 | 2 | $2C_4H_4O_4$ | 163° C |
| 36 | $COOC_2H_5$ | p F | $nC_3H_7$ | 2 | 2 | 2 HCl | 160° C |

The derivatives according to the invention can also be identified by their infra-red and nuclear paramagnetic resonance spectra.

According to a first embodiment of the process for the preparation of derivatives of group I, a monosubstituted benzhydryloxyalkyl piperazine is reacted in an organic solvent under reflux and in the presence of a hydracid acceptor with a halogenated compound having the formula $X(CH_2)_{n'}A$, X being a halogen atom and n' and A being as defined above.

The reaction can be written as follows:

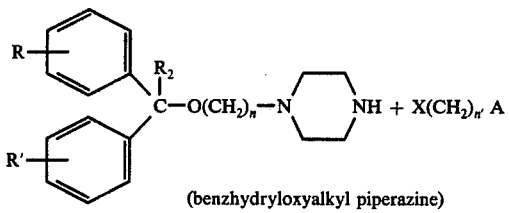

(benzhydryloxyalkyl piperazine)

The organic solvent, for example, can be ethanol and the hydracid acceptor can be sodium bicarbonate.

In order to prepare the derivatives of group I wherein n' is equal to 2, the halogenated derivative $X(CH_2)_{n'}A$ can be advantageously replaced with an acrylic derivative having the formula $CH_2=CH-A$.

In such a case, the above-mentioned reaction can be carried out directly in the hot, in the solvent, without any hydracid acceptor.

According to a second embodiment of the process for producing derivatives according to the invention, in order to prepare the derivatives of group I, benzhydryl and omega-chloroalcoyl oxide having the formula:

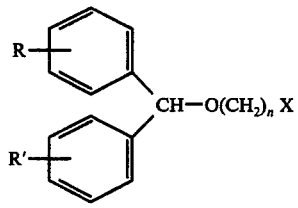

is reacted in an organic solvent in the hot and in the presence of a hydracid acceptor, with the monosubstituted piperazine having the formula:

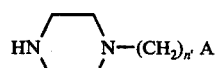

wherein R, R', n, X, n' and A are as defined above.

The organic solvent, for example, can be toluene and the hydracid acceptor can be triethylamine.

The halogenated compound having formula (IV) can be used to prepare the monosubstituted piperazine derivative having formula (III) by reacting compound (IV) under reflux with an excess of piperazine in a solvent such as xylene.

According to a third embodiment of the process for producing derivatives according to the invention, in order to prepare the derivatives of group I, in the presence of potassium tert-butoxide and tert-butyl alcohol, the compound having the formula:

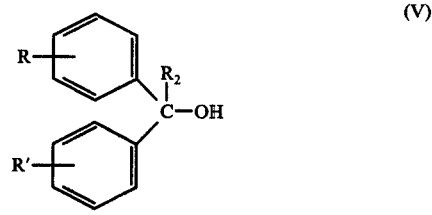

is reacted with the disubstituted piperazine having the formula:

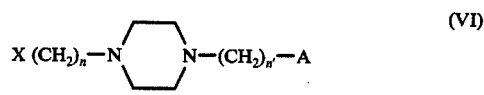

wherein X is a halogen and n, n' and A are as defined above.

The oxygen in compound (V) provides a bond with the $-(CH_2)_n-$ group of compound (VI) whereas halogen X, which is preferably chlorine, is liberated as a hydracid HX.

In order to prepare the derivatives of group II, the following procedure is preferably used: The phenylketone, having the formula

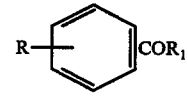

is reacted with ethylene glycol which gives a cyclic ketal and the latter is then reduced under mild conditions in a basic solvent to an etheralcohol having the formula:

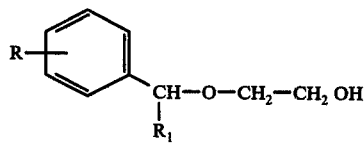

this compound is converted to a halide using an alcohol halogenating agent and the halide obtained is then reacted with the monosubstituted piperazine having the formula:

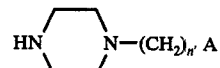

as in the second embodiment of the process for the preparation of the derivatives of group I.

The reaction can be written as follows:

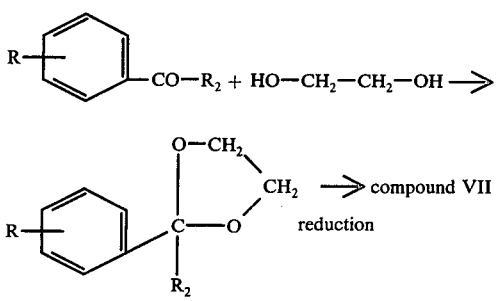

Several non-limiting examples for the preparation of derivatives useful as active substance in pharmaceutical compositions according to the invention are given below:

EXAMPLE 1:

Preparation of 1-(methoxycarbonylbutyl)-4-[2-(4,4'-difluorobenzhydryloxy)ethyl]piperazine dihydrochloride (derivative n° 14 in Table I).

To a solution of 0.05 mole of 1-[2-(4,4'-difluorobenzhydryloxy)ethyl]piperazine, i.e., 16.6 g, in 50 ml of ethanol, prepared, for example, according to the general procedure described in Industrie Chimique Belge, volume XXII, p. 416, 1957, which consists in reacting in xylene, under reflux, a reactive halogen derivative with 3 to 4 times the theoretical quantity of anhydrous piperazine, were added, in succession, 0.05 mole (4.2 g) of sodium bicarbonate and 0.05 mole of methyl omega-bromovalerate (9.8 g). The mixture was refluxed with stirring for 8 hours. The insoluble material was filtered off, the alcohol stripped, the residue extracted with benzene and the benzene extract washed with water until neutral. The solvent was dried and evaporated.

18 g of a pure product were obtained which were converted directly to the hydrochloride by reaction with HCl and recrystallized from isopropyl alcohol. The melting point of the product obtained was 200° C. The yield of this preparation was 80%.

EXAMPLE 2

Preparation of 1-(morpholinocarbonylmethyl)-4-[2-benzhydryloxyethyl]piperazine dimaleate. (derivative n° 31).

The procedure of example 1 was employed using a substantially stoichiometric quantity of morpholinochloroacetamide, the product obtained being converted to the dimaleate. The product had a melting point of 205° C. The yield was 93%.

EXAMPLE 3

Preparation of 1-(piperonylpiperazinocarbonylmethyl)-4-(2-benzhydryloxyethyl)piperazine trimaleate. (derivative n° 33).

The procedure of example 1 was employed using a stoichiometric quantity of piperonylpiperazine chloroacetamide, the product being converted to the trimaleate. The product obtained had a melting point of 190° C. The yield was 89%.

EXAMPLE 4

Preparation of 1-(carboxyethyl)-4-(2p-fluorobenzhydryloxyethyl)-piperazine dimaleate (derivative n° 5).

To a solution of 0.04 mole of 1-(2p-fluorobenzhydryloxyethyl)piperazine (12.6 g) in benzene, was added 0.05 mole of ethyl acrylate. The mixture was heated for 2 hours under reflux. The solvent and excess acrylate were stripped off. The residual oil was extracted with 50 ml of methanol and 12 ml of 4N of sodium hydroxide. The alcohol was refluxed for two hours. It was neutralized with 12 ml of 4N HCl. The methanol was evaporated, the residue extracted with 100 ml of chloroform and washed twice with 50 ml of water. The solvents were dried and stripped off. 14.8 g of product were obtained which is a 95% yield. The amino-acid thus obtained was then dissolved in the minimum quantity of methanol in the hot and a warm solution of 9.3 g of maleic acid (0.8 mole) in methanol was added. The dimaleate precipitated and was recrystallized from methanol. 17 g of product were obtained with a melting point of 175° C.

EXAMPLE 5

Preparation of 1-(m-hexyloxycarbonylethyl)-4[2-(4,4-difluorobenzhydryloxy)ethyl]piperazine dimaleate. (derivative N° 26).

The procedure of example 4 was employed using hexyl acrylate instead of ethyl acrylate, without saponification of the ester. The product obtained had a melting point of 174° C. The yield was 83%.

EXAMPLE 6

Preparation of 1-(propionitrile-4-(2-benzhydryloxyethyl)piperazine dihydrochloride. (derivative N° 29).

The procedure of example 4 was employed using acrylonitrile instead of ethyl acrylate. The product obtained had a melting point of 160° C. The yield was 92%.

EXAMPLE 7

Preparation of 1-(ethoxycarbonylethyl)-4-(3-p-fluorobenzhydryloxypropyl)piperazine dihydrochloride (derivative N° 28).

The procedure of example 4 was employed using 1-(3p-fluorobenzhydryloxypropyl)piperazine without saponification of the ester. The product obtained had a melting point of 200° C. The yield was 87%.

EXAMPLE 8

Preparation of 1-(carboxyethyl)-4-(2,0-methoxybenzhydryloxyethyl)piperazine dimaleate. (derivative N° 7).

To a 100 ml toluene solution of 0.05 mole of 2-chloroethyl and 0-methoxybenzhydryl oxide, prepared, for example, according to the method described in Organic Synthesis 33, 11, were added 0.05 mole of triethylamine and 0.05 mole of 1-(ethoxycarbonyl-ethyl)piperazine. The mixture was refluxed for 8 hours, the toluene was then stripped off and the residue extracted with 200 ml of benzene. The benzene solution was washed twice with a 20 ml solution of 15 ml acetic acid and 250 ml of water. It was then dried and evaporated under vacuum. 31 g of ester were obtained which were treated with methanol and maleic acid as in example 4. The product obtained had a melting point of 175° C.

EXAMPLE 9

Preparation of 1-(carboxyethyl)-4-(2,0-methoxybenzhydryloxyethyl)piperazine dimaleate. (derivative N° 7).

To a solution of 10.7 g (0.05 mole) of O-methoxybenzhydryloxylethyl in 150 ml of tert-butyl alcohol, were added 5.6 g (0.05 mole) of potassium tert-butoxide. The mixture was refluxed for 30 minutes and 12.4 g (0.05 mole) of 1-(ethoxycarboxyethyl)-4-(2-chloroethyl)piperazine were added at this temperature. Heating was continued for 30 minutes. The mixture was then poured into 200 ml of water and extracted with methylene chloride. 15 g of ester were obtained which were then treated with methanol and maleic acid as in Example 4. The product obtained had a melting point of 175° C. The yield was 65%.

EXAMPLE 10

Preparation of 1-(ethoxycarbonylethyl)-4-[2-butoxy-1-p-fluorophenyl)ethyl]piperazine dihydrochloride. (derivative N° 36 in Table II).

p-fluorobutyrophenone was treated with ethylene glycol in order to convert it into 2-(n-butoxy-1-paraphenyl)ethanol. This alcohol was converted to the chlorinated derivative, for example, through the action of thionyl chloride in the presence of pyridine in 83% yield. 1-(2-n-butoxy-1-p-fluorophenyl)ethyl)piperazine was prepared in 70% yield by reacting 2-(n-butoxy-1-p-fluorophenol)-1-(chloro)ethane with piperazine in refluxing xylene using 3 to 4 times the theoretical quantity of piperazine. The monosubstituted piperazine derivative thus obtained was reacted with ethyl acrylate as in Example 4. The product obtained had a melting point of 160° C.

The pharmaceutical compositions of the present invention containing these new piperazine derivatives and their salts, in particular, the hydrochlorides and maleates, are useful in human and veterinarian therapy.

The derivatives comprising the active substance of the pharmaceutical compositions according to the invention have an essentially phychostimulating activity which is associated, as far as some of them are concerned, with a spasmolytic activity of the papaverine type.

Acute toxicity and psychostimulating and spasmolytic activities.

In the following Table are shown the results of pharmacological tests carried out on derivatives 1 to 36 corresponding to those shown in the above-mentioned Tables I and II.

Acute toxicity was studied by determining the $LD_{50}$ in mice, the derivatives being administered per os.

The psychostimulating activity was studied by determining the dose which increases the exploration response in mice (actimetry) by 50% ($ED_{50}$), according to the method described by BOISSIER J.R. and SIMON P. (Arc. Int. Pharmacolyn, 1965, 212–221158).

The papaverine spasmolytic activity was measured "in vitro" by the concentration ratio: active principle/papaverine hydrochloride concentration, which reduces duodenum contractions in rats, induced by barium chloride, by 50% according to the method of POMARET J. C., SERGANT – ODY M., POURRIAS B. and HUGUET G. (Therapie, 1969, 24, 109–143).

TABLE III

| Derivative n° | $LD_{50}$ (mg/kg/per os) | Psychostimulating activity $ED_{50}$ mg/kg/per os | Spasmolytic activity (papaverine hydrochloride = 1) |
|---|---|---|---|
| 1 | >1600 | 400 | 0 |
| 2 | 2250 | 80 | 0 |
| 3 | 1500 | 80 | 0 |
| 4 | 1600 | 60 | 0 |
| 5 | 800 | 22 | 0 |
| 6 | 1200 | 200 | 0 |
| 7 | 1400 | >400 | 0 |
| 8 | 1000 | 30 | 0 |
| 9 | 1400 | 100 | 0 |
| 10 | >1600 | >400 | 0 |
| 11 | 700 | 30 | 0,1 |
| 12 | 1200 | 35 | 0,1 |
| 13 | 1400 | 35 | 0 |
| 14 | 500 | 45 | 3,5 |
| 15 | 1200 | 40 | 6,5 |
| 16 | 2000 | 100 | 1,5 |
| 17 | 1600 | >200 | 1,5 |
| 18 | 1400 | 30 | 1 |
| 19 | >1600 | >400 | 1,5 |
| 20 | >1600 | >400 | 5,5 |
| 21 | 750 | 30 | 8,5 |
| 22 | >1600 | 35 | 5,5 |
| 23 | 800 | 50 | 13,5 |
| 24 | 700 | 50 | 2,5 |
| 25 | 500 | 40 | 0,5 |
| 26 | 800 | 200 | 1 |
| 27 | 800 | 50 | 3,5 |
| 28 | 800 | <100 | 6,5 |
| 29 | 300 | 40 | 1 |
| 30 | 1000 | 80 | 0,1 |
| 31 | 800 | 100 | 0,5 |
| 32 | 1200 | 100 | 2 |
| 33 | 600 | 25 | 10,5 |
| 34 | >1600 | 160 | 1,5 |
| 35 | >1600 | 60 | 0 |
| 36 | 1600 | >100 | 5 |

In Table IV are shown, by way of examples, several pharmacological properties of derivatives N° 2, 3, 5, 16 and 21 which have the smallest $ED_{50}/LD_{50}$ ratio and are devoid of any secondary action on the dog cardiovascular system through intravenous administration.

These compounds, from the pharmacological point of view, are non-amphetamine psychostimulants.

TABLE IV

| Pharmacological Activity | Derivative n° 2 | 3 | 5 | 16 | 21 |
|---|---|---|---|---|---|
| Group toxicity: $LD_{50}$ grouped mice $LD_{50}$ isolated mice | 0,6 | 1,25 | 0,6 | 0,8 | 0,4 |
| Potentiation of mortality with pentetrazole in mice $ED_{50}$ (mg/kg/per os) | 320 | >300 | 160 | >400 | >100 |
| Anticataleptic action in rats AD (mg/kg/per os) | 200 | 150 | 150 | >200 | <80 |
| Ptose antagonism with reserpine in mice $ED_{50}$ (mg/kg/per os) | 55 | 160 | 100 | 190 | 70 |
| Anti-sleep activity in mice | Nil | Nil | Nil | Nil | Nil |

As an example, for derivative N° 5, two other pharmacological properties were revealed:
- absence of anorectic action in rats
- increase in aggressiveness in mice in the electric struggle test where the $ED_{50}$ is 6.5 mg/kg per os.

Derivative N° 5 was found to have a low chronic toxicity for it is well tolerated by rats when administered orally 6 out of 7 days at a daily dose of 80 mg/kg.

Table V below gives, by way of example, the complementary pharmacological activities such as antiserotonin, adrenolytic and atropinic activities for derivatives N° 21, 23 and 33, the spasmolytic activity of which is the greatest for the rat isolated duodenum. For compound 21 which was found to have an excellent spasmolytic activity of the papaverine type in the tests as a whole, a chronic toxicity study carried out as an example showed that the dose of 40 mg/kg per os, administered 6 out of 7 days, for six months, is perfectly well tolerated by rats.

TABLE V

| Pharmacological activity | Compound n° | | |
|---|---|---|---|
| | 21 | 23 | 33 |
| In vitro spasmolytic action wpm tje rabbot aprta- (papaverine hydrochloride = 1) | | | |
| In vitro spasmolytic action on the rabbit isolated ear- (papaverine hydrochloride = 1) | 1,5 | 0,3 | 0,5 |
| In vivo spasmolytic action on paw vessels of the dog: (papaverine hydrochloride = 1) | 30 | 2 | 9 |
| In vitro anti-serotonin activity on the female rat uterus in oestrus: (Methysergide = 1) | 0,07 | 0,015 | 0,015 |
| In vitro adrenolytic action on the Guinea-pig seminal vesicle: (Yohimbinehydrochloride = 1) | 4 | 3 | 6 |
| In vitro atropinic action on the Guinea-pig ileum: (Atropine sulfate = 1) | >0,01 | >0,01 | >0,01 |

Therapeutic action:

By way of example, clinical tests were carried out on derivatives N° 5 and 21.

Derivative N° 5 was administered at a dose of 30 mg daily in three oral administrations of 10 mg to 6 adults treated for neurotic depression, neurasthenia and school overwork. The following results were obtained after treatment for one month:

| Results | Neurotic depression | Neurasthenia | School overwork |
|---|---|---|---|
| Excellent | 1 | | 2 |
| Good | 1 | | 1 |
| Nil | | 1 | |
| Number of cases | 2 | 1 | 3 |

The presence of a phychostimulating action was therefore shown 5 out of 6 times.

Derivative 21 was administered at a dose of 15 mg/day in three 5 mg portions orally to adults suffering from arteritis of the lower limbs, cerebral vascular sclerosis, sequelae of hemiplegia and who all showed a counter-acting depressive state, in relation with a poor acceptance of their physical state.

The results after one month of treatment were as follows:

| Arteritis of the lower limbs | 8 cases |
|---|---|
| Improvement of the walking perimeter | 6 times |
| Improvement of the psychic state | 4 times |
| Cerebral vascular sclerosis | 4 cases |
| Improvement in intellectual activity | once |
| Improvement of the psychic state | twice |
| Hemiplegia sequelae | 2 cases |
| Improvement of motor disturbances | 0 |
| Improvement of the psychic stae | once |

Therapeutic indications:

The results of the pharmacological and clinical tests carried out on the derivatives according to the invention give, in particular, the following therapeutic indications: - counter-acting neurotic depressions, neurasthenias, professional or school overwork, psychosomatic fatigue and disturbances connected with peripheral or central vascular failure (arteritis of the lower limbs, senescence).

Dosage

The pharmaceutical compositions containing the derivatives according to the invention as active substances can be administered as capsules, tablets, drinkable or injectable ampoules or suppositories containing a medicinal dose of active substance ranging from 5 to 25 mg.

The preferred dosage is:
- for adults, from 10 to 20 mg of active substance daily
- for children, from 5 to 15 mg daily.

Examples of formulations of the medicines according to the invention are given below:

EXAMPLE I

| Capsules | |
|---|---|
| 1-(carboxyethyl)-4-(2-p-fluorobenzhydryloxyethyl)-piperaine dimaleate (derivative n° 5) | 10 mg |
| granulation vehicle | q.s.p. |
| or 1-(ethoxycarbonylethyl)-4[2(4,4'-difluorobenzhydryloxy)-ethyl]piperazine dihydrochloride (derative No 21) | 5 mg |
| granulation vehicle | q.s.p. |

EXAMPLE II

| Tablets | |
|---|---|
| derivative n° 5 | 10 mg |
| compression vehicle (talcum, starch, stearate) | q.s.p. |
| or derivative n° 21 | 5 mg |
| compression vehicle | q.s.p. |

EXAMPLE III

| Drinkable ampoules | |
|---|---|
| derivative n° 5 | 15 mg |
| aromatized vehicle q.s.p. | 10 ml |

EXAMPLE IV

| Injectable ampoules | |
|---|---|
| derivative n° 21 | 10 mg |
| saline solution q.s.p. | 10 ml |

EXAMPLE V

| Suppositories | | |
|---|---|---|
| derivative n° 5 | 15 | mg |
| semi-synthetic glycerides q.s.p. | 2.10 | g |
| or derivative n° 21 | 10 | mg |
| semi-synthetic glycrides q.s.p. | 2.10 | g |

We claim:

1. A pharmaceutical composition of nonamphetaminic psychostimulating activity comprising as active substance a 1,4-disubstituted piperazine of the formula:

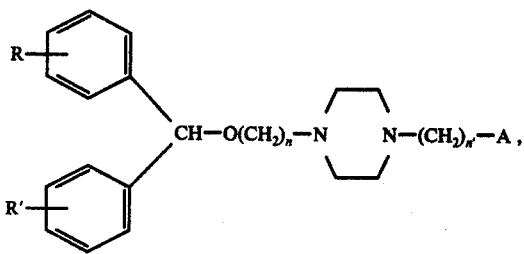

wherein R and R' are identical or different and are hydrogen or fluorine, n being equal to 2, n' being equal to 2 or 3 and A being selected from the group consisting of COOH, COONa, COOCH₃ and COOC₂H₅, in a pharmaceutically acceptable carrier.

2. A pharmaceutical composition according to claim 1, wherein the piperazine derivative is salified by a pharmaceutically acceptable acid.

3. A pharmaceutical composition, according to claim 1, and comprising as active substance 1-(carboxyethyl)-4-(2-p-fluorobenzhydryloxyethyl)-piperazine.

4. A pharmaceutical composition according to claim 1, and comprising as active substance 1-(ethoxycarbonyl-ethyl)-4[2(4,4'-difluorobenzhydryloxy)-ethyl]piperazine.

* * * * *